United States Patent [19]

Gardner et al.

[11] Patent Number: 4,483,757

[45] Date of Patent: Nov. 20, 1984

[54] PHOTOCHEMICAL PROCESS FOR PREPARING AMINES

[75] Inventors: David M. Gardner, Worcester; Paul J. McElligott, Abington, both of Pa.

[73] Assignee: Pennwalt Corporation, Philadelphia, Pa.

[21] Appl. No.: 601,831

[22] Filed: Apr. 19, 1984

Related U.S. Application Data

[63] Continuation-in-part of Ser. No. 333,941, Dec. 23, 1981, Pat. No. 4,459,191, which is a continuation-in-part of Ser. No. 259,731, May 1, 1981, abandoned, which is a continuation-in-part of Ser. No. 143,989, Apr. 28, 1980, abandoned.

[51] Int. Cl.³ .............................................. B01J 19/12
[52] U.S. Cl. .............................. 204/158 R; 204/162 R
[58] Field of Search ............ 204/158 N, 162 R, 158 R

[56] References Cited

U.S. PATENT DOCUMENTS 3,491,008  1/1970  Broaddus ........................ 204/158 R Primary Examiner—Howard S. Williams

[57] ABSTRACT

Aliphatic, cycloaliphatic, heterocyclic aliphatic and aromatic amines are prepared in a liquid phase reaction under the influence of light energy in the presence of a specified ammonium halide photocatalyst whereby addition of N—H bonds from ammonia or a primary or secondary amine occurs across the double bond of an olefin.

11 Claims, No Drawings

PHOTOCHEMICAL PROCESS FOR PREPARING AMINES

This application is a continuation-in-part of copending application Ser. No. 333,941, filed Dec. 23, 1981, now U.S. Pat. No. 4,459,191, which is a continuation-in-part of application Ser. No. 259,731, filed May 1, 1981, now abandoned, which is a continuation-in-part of application Ser. No. 143,989, filed Apr. 28, 1980, now abandoned.

BACKGROUND OF THE INVENTION

This invention relates to a method for preparing aliphatic, cycloaliphatic, heterocyclic aliphatic and aromatic amines from olefins and ammonia or primary or secondary amines whereby N—H bonds are added across the double bond of the olefin by the influence of actinic light and a specified ammonium halide photocatalyst. Amines are widely used commercially as intermediates in the manufacture of rubber products, pharmaceuticals, insecticides, dyestuffs, textile finishing agents and other products.

PRIOR ART

Prior art methods for preparing amines have either involved reduction of nitriles, nitro compounds, etc. or reactions in which the amino group replaces some other functional group, such as the hydroxyl group in alcohols, the chloro or bromo group in alkyl chlorides or bromides, the oxygen in the carbonyl group of aldehydes or ketones or an alkoxy group in ethers. Direct synthesis of amines from olefins bypasses the need for these intermediate compounds containing functional groups and simplifies the isolation and purification of the desired product amines.

U.S. Pat. No. 2,772,271 discloses a method for reacting amines and alpha-olefins in the presence of peroxides or light that results in addition of the olefin at an alpha carbon atom of the amine. Similarly, U.S. Pat. No. 3,492,353 contains a disclosure of an analogous reaction in which the amine is trimethylamine and which is conducted in the presence of a free-radical catalyst or actinic radiation of a quartz discharge lamp [which emits above 224 nm (nanometers)]. This reaction likewise leads to addition of olefin molecules to the carbon atoms alpha to the amino nitrogen. D. Bryce-Smith et al. [Angew. Chem., Int'l Ed., 13, 341 (1974)] report 1, 2- and 1,3- photoaddition of primary and secondary amines to benzene. F. D. Lewis and T. Ho [JACS 99, 7991 (1977)] and M. Kawanisi and K. Matsunaga [J. Chem. Soc. Chem. Commun. 313 (1972)] report the photochemical addition of dialkylamines to the activated olefin stilbene to form, among other products, N, N dialkyl-1,2-diphenylethylamine, in low yields (15-20%). Lewis and Ho used low energy monochromatic light (313 nm) and apparatus which transmits wavelengths only above about 290 nm. The reaction of ammonia with benzene, toluene, or xylene under the influence of a nondisruptive electric discharge or irradiation by actinic light to form aniline, toluidine, and xylidine, respectively, plus hydrogen as disclosed in U.S. Pat. No. 2,749,279, does not involve addition across a double bond.

STATEMENT OF THE INVENTION

The present invention is directed to a process for producing amines comprising reacting in the liquid phase, under the influence of light having an emission spectrum beginning above 160 nm and in the presence of ammonium iodide or ammonium bromide photocatalyst, a primary or secondary amine or ammonia with an olefin having one or more non-aromatic carbon to carbon double bonds whereby an N—H bond of the amine or ammonia is added across the double bond of the olefin.

DISCUSSION OF THE INVENTION

The process of the present invention can be illustrated by the following general reaction:

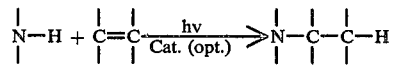

This process is conducted with ammonium iodide or bromide photocatalyst and an artificial source of actinic radiation having significant output on the spectral region with emissions beginning above about 160 nm.

Since the reactors and lamps used for this purpose usually consist of vessels having conventional quartz glass walls to pass actinic light, the lower-wavelength end, in practice, is usually set by the light transmission cut-off of conventional quartz glass (around 180 nm). The use of amorphous silica or synthetic silica glass (cut-off around 160 nm) to replace the quartz glass of the vessel walls or the lamp glass of the equipment of this process is advantageous (although more expensive) because it transmits more short-wave length ultraviolet radiation than conventional quartz glass. Glass comprising such synthetic silica is marketed under the trademark Suprasil by Heraeus Amersil and as Corning #7940 by Corning Glass Company.

Typical examples of lamps emitting in the range of 160–200 nm are deuterium lamps, low-pressure mercury-argon lamps, and high-energy xenon flash lamps. The high-energy xenon flash lamp is particularly effective because of its high-energy intensity and its large output in the range 180–220 nm. Lamps producing emissions in the higher spectral regions including high pressure mercury lamps emitting in the 200 to 1400 nm range, are also effective sources of actinic light.

The photocatalyst referred to herein would respond to light below 160 nm; however, such radiation is out of the range of practicality. At the present time even the finest grade of quartz glass has only a very small transmission at, and below, 160 nm. In addition, the cost of lamps to generate radiation of this, and shorter, wavelengths is prohibitively expensive.

While the light-catalyzed reaction of this invention would occur if the reactants were to be exposed for a sufficient period of time to direct sunlight, this form of actinic radiation is so low in intensity without some artificial means of concentrating the radiation that the process would have no practical value.

The photocatalysts of this invention are ammonium iodide and ammonium bromide. These halides can be used in any catalytically effective amount with respect to the amine or ammonia reactant, the preferred amount ranging from at least 0.01 mol/mol of amine or ammonia up to the limit of solubility of the halide in the amine or ammonia reactant. In general, the mole ratio of ammonia or amine to photocatalyst is 20:1 to 500:1 with a ratio of 100:1 to 400:1 being preferred. The specified photocatalysts can be used individually or in combination to improve conversions and yields. The preferred photocatalyst is ammonium iodide. It has been found that any light-absorbing ketone impurity which may be present in the ammonium halide as a result of its method of manufacture must be removed, usually by salt recrystallization, since such impurity substantially affects the olefin conversion to amine.

The term "ammonium iodide and ammonium bromide photocatalyst" as used herein includes iodide or bromide compounds which react with ammonia under the conditions of the process disclosed herein. For example, alkyl iodides or bromides, reactive metal iodides or bromides, e.g., ferric iodides, ferric bromide, tin iodide, silicon bromide and the like will, with ammonia, form the respective ammonium halide which will enter the amination cycle to produce amines from olefins.

It has been found that ammonium chloride and ammonium fluoride are promoters and not true catalysts since their use produces no more than a stoichiometric yield of amine product. In addition, the use of ammonium chloride results in a product amine in the form of a hydrochloride salt and it is difficult to free the amine product under the conditions of the process to recover the amine and possibly, to recycle the resulting ammonium chloride salt.

Suitable reactants containing N—H bonds are ammonia and the various primary and secondary amines. Specific examples of such amines include methylamine, dimethylamine, ethylamine, diethylamine,n-propylamine, isopropylamine, di(n-propyl) amine, di(isopropyl) amine, n-butylamine, di (n-butyl) amine, sec-butylamine, di-(sec-butyl) amine, isobutylamine, di(isobutyl) amine, the pentyl and higher alkyl amines; cycloaliphatic amines such as cyclohexylamine; aromatic amines such as aniline, the N-alkylanilines, diphenylamine, the naphthylamines, and the toluidines; heterocyclic amines such as pyrrolidine, morpholine, and piperidine; substituted amines such as the alkanolamines; and polyamines such as ethylene diamine, and 1,6-hexanediamide.

Preferred N—H containing reactants, because of their commercial significance, are ammonia, and the mono- and di-alkyl ($C_1$–$C_6$) amines. An especially preferred N—H containing reactant is ammonia.

Olefinic compounds suitable for the present process include those having one or more non-aromatic carbon-carbon double bonds, internal and/or terminal. Specific examples of such compounds are ethylene, propylene, 1-butene, 2-butene, isobutylene, 1-pentene, 2-pentene, 3-methyl-1-butene, 2-methyl-1-butene, 2-methyl-2-butene, the several possible hexenes, higher alkenes (e.g., dodecene), cyclobutene, cyclopentene, cyclohexene, cycloheptene, cyclopentadiene, cyclohexadiene, cyclooctadiene, butadiene, 2-methyl-1,3-butadiene, 2-chloro-1,3-butadiene, cyclododecatriene, acrylonitrile, vinyl chloride, methylvinyl ether, allyl alcohol, and furan.

Double bonds adjacent to groups that can stabilize free-radicals are said to be activated, and these generally react much more readily than unactivated double bonds.

Preferred olefins for our process, because of their commercial significance, are the unactivated alkenes of 2 to 18 carbons. Ethylene is particularly preferred based on the usefulness of the amines produced therefrom.

It is understood that the N—H containing reactants and olefins can be optionally substituted with various groups (such as —OH, -halide, —CN) as long as such groups do not interfere with the process.

Temperatures for conducting the process of this invention range from above the freezing temperature of the reactants to about 40° C. and any convenient temperature within the range may be used. Temperatures in the range −10° C. to 10° C. are preferred. The lower temperatures allow greater solubility of gaseous olefins, such as ethylene, in liquid ammonia or the amines.

The ratio of amounts of olefin and amine or ammonia reactants can vary over a wide range depending on which reactant is employed in excess and functions as the reaction medium. In general, it is more suitable to use the amine in excess since an excess of olefin can lead to losses by polymerization induced by the ultraviolet light. The mole ratio of ammonia or starting amine to olefin can range from 1:1 to 50:1 with a ratio in the range of 5:1 to 15:1 being preferred.

The reaction is carried out in the liquid phase and the total pressure, which is a combination of the vapor pressures of the ammonia or amine and the olefin, can range from near atmospheric to over 600 psig. The usual range is from about 0 psig to about 500 psig.

The solubility of olefins in the liquid ammonia or liquid amine containing the ammonium halide catalyst is usually low and to improve the solubility of the olefin, in order to improve the reaction rate, inert solubilizing agents have been employed of the type which are commonly used to disperse relatively non-polar organic materials in polar inorganic or organic solvents. Examples include alkyl-or aryl-substituted ammonium, phosphonium, or sulfonium salts which do not decompose under the influence of ultraviolet light or react with any of the reactants. The materials preferred for use are tetralkylammonium iodides or tetraalkylammonium bromides especially tetra-n-butyl ammonium iodide, tetra-n-butyl ammonium bromide and tetra-n-heptyl ammonium iodide.

EXAMPLES

The examples which follow illustrate the process of this invention as carried out in equipment which may be used in a continuous process in either the liquid or gas phase with known methods for introducing reactants and the photocatalyst, and for separating products from the starting materials.

In each of Examples 1–8, the ultraviolet light source was a 550-watt, high pressure mercury lamp produced by Canrad-Hanovia, Inc. The lamp has an emission spectrum from below 222.4 nm to over 1,367.3 nm. The reactants were premixed to insure proper mixing and to cool the mixture to about 7°–8° C. in the mixing chamber by circulation in the dark for 0.5 hour (Example 7, for 1 hour) and then the reactant mixture was irradiated under the light source for four hours.

The reactions of the examples were carried out in an air-free and moisture-free environment. The apparatus was cleaned, dried, and purged with pure nitrogen prior to adding the reactants. The space between the reactor and the reflecting cylinder containing the mercury lamp was also purged with nitrogen to avoid the loss of ultraviolet light through its absorption in ozone which may be formed in the presence of oxygen.

Each product amine of Examples 1–8 was identified by gas chromatographic analysis, infrared spectrophotometric analysis, proton nuclear magnetic resonance spectrometric analysis, and $F_{19}$-nuclear magnetic resonance spectrometric analysis of the hexaflouroacetone derivative. All the ethylamines and propylamines were isolated by bulk distillation of the product mixtures and a majority of the liquid products underwent elemental analyses. Analysis results are reported as "percent conversion" and "percent yield". "Percent conversion" is the percent of the olefin charged which has undergone reaction. "Percent yield" is the percent of the olefin reaction product which has formed the desired amine. "Percent yield" takes into consideration the possible conversion of some olefin to undesirable by-product.

EXAMPLE 1

Ammonium iodide, 0.068 moles, dissolved in 18.2 moles of ammonia was charged into a circulating reactor system consisting of a 30 cm. tall, one-liter stainless steel cylindrical reservoir, which serves as a mixing and cooling chamber, a 24 cm. tall, 2.5 cm. O.D. reactor with quartz walls for admitting the actinic light to the solution, and a circulating pump. External to the quartz reactor was a high pressure mercury lamp. Both reactor and lamp were enclosed in a 76 cm. tall, 18 cm. O.D. reflecting stainless steel cylinder. Ethylene was then charged into the system until the pressure reached 250 psig and it was found that 6.4 moles of ethylene were dissolved in the ammonia. No reaction was observed during the mixing period. The circulating high pressure (autogenous) liquid reactant mixture was then exposed to the ultraviolet light of the mercury lamp. Analysis of the reaction mixture after irradiation showed a 6% ethylene conversion and a 99+% yield to monoethylamine.

EXAMPLE 2

Ammonium iodide, 0.068 moles, was dissolved in 11.8 moles of ammonia and the mixture charged into the reactor system described in Example 1 following the initial addition of 2.38 moles of propylene and 0.014 moles of tetra-n-butylammonium iodide (to promote the solubility of propylene in the liquid ammonia phase). The system was brought to a pressure of 250 psig with nitrogen to prevent cavitation in the circulating pump (autogenous pressure was 170 psig at 7° C.). After irradiation, analysis of the product mixture showed a 3% conversion of propylene with a 99+% yield of n-propylamine.

EXAMPLE 3

A mixture of 11.8 moles of ammonia, 1.64 moles of isobutylene, and 0.068 moles of ammonium iodide was charged into the reactor system described in Example 1. In addition, 0.014 moles of tetra-n-butyl-ammonium iodide was added to promote the solubility of isobutylene in the liquid ammonia phase. After irradiation of the liquid mixture, whose pressure of 250 psig was maintained by nitrogen, analysis of the product mixture showed a 1.3% conversion of isobutylene and a 99+% yield of isobutylamine.

EXAMPLE 4

A mixture of 1.2 moles of cyclohexene, 11.8 moles of ammonia, and 0.068 moles of ammonium iodide were charged into the reactor system described in Example 1. 0.014 moles of tetra-n-butylammonium bromide was also added to promote the solubility of cyclohexene in the liquid ammonia phase. The high pressure (250 psig) was maintained by the addition of nitrogen. After irradiation, analysis of the product mixture showed a 3.4% conversion of cyclohexene to cyclohexylamine.

EXAMPLE 5

A mixture of 6.6 moles of dimethylamine, and 0.069 moles of ammonium iodide was charged into the reactor system described in Example 1. Ethylene was charged into the system until the pressure reached 250 psig and 0.64 moles dissolved into the solution. After exposure to the U. V. light, analysis of the resulting product solution indicated a 4.1% conversion of ethylene and a 99+% yield of dimethylamine.

EXAMPLE 6

Ammonium bromide, 0.102 moles, was dissolved into 26.47 moles of ammonia and the mixture was charged into the reactor system described in Example 1. Ethylene was then charged into the system until the pressure reached 250 psig; under these conditions, it was found that 0.38 moles of ethylene was dissolved in the ammonia phase. Following exposure to the actinic light, analysis of the mixture indicated a 9% conversion of ethylene and a 98+% yield of monoethylamine.

EXAMPLE 7

1.00 mole of ammonium iodide dissolved in 90.5 moles of ammonia was charged into a three-liter storage cylinder attached to a single-pass, pressurized-feed reactor system consisting of a trickle bed chiller system to saturate the ammonia with ethylene, a one-inch O.D., 24 inch long tube type quartz reactor for admitting actinic light, flow controllers for liquid ammonia and gaseous ethylene and a stainless steel receiver to retain the product mixture. A reflecting cylinder enclosed both the reactor system and the high pressure mercury lamp as described in Example 1. The system was pre-pressurized with ethylene to 200 psi and the ammonia-ammonium iodide solution was fed to the system at a rate of 2 to 200 mls per minute. Under these conditions, a total of 0.64 moles of ethylene was dissolved in the ammonia-ammonium iodide solution. It was calculated that the flowing solution was exposed to the ultraviolet light for one hour and thus resulted in an average ethylene conversion of 6 to 10% and an average of 90+% yield of monoethylamine. The optimum gaseous ethylene flow range was 1 to 2000 cc/min (STP) and the optimum ammonia-ammonium iodine solution flow rate was 0.01 to 200 cc/min. The product mixture was routinely distilled to recover the amine.

EXAMPLE 8

Example 7 was repeated except that the system was pre-pressurized with ethylene to 260 psi. This procedure resulted in an average of ethylene conversion of 6 to 10% and an average of 90+% yield of mono and diethylamine in a molar ratio of 7:1 and a small undetermined amount of triethylamine.

EXAMPLE 9

This example reports in the table below yields of N-t-butylcyclohexylamine obtained for two reactions of 1.48 moles of tertiary butylamine with 0.3 moles of cyclohexene at atmospheric pressure, a temperature within the range of 30 to 40° C. and a reaction time of 21 hours with and without the presence of a catalyst (ammonium iodide). The reactions were carried out in a laboratory quartz reactor (Ace Glass Inc., Vineland, N.J.—Catalog No. 7840) having a 250 ml. capacity. Nitrogen was bubbled through the reaction mixture during the process and the mechanical stirrer was operated at medium speed. The light energy for the reaction was supplied by a 450-Watt Hanovia U. V. lamp (Catalog No. 6515-34/6531-14). 47.6% of the total energy of this lamp is radiated in the U. V. spectral region ranging from 222.4 to 366.0 nm.

The overall-yields for these two reactions differ from the yields given in the previous examples in that the overall-yields can be considered a product of conversion and yield. The overall-yields were obtained by gas chromatographic analysis where the peak area for the product in the reaction mixture was compared to the peak area of an amount of actual product in a synthetic sample. Equal volumes of product samples were injected into the gas chromatograph (thermal conductivity detector).

TABLE 1

| Reaction No. | Catalyst or Sol. Agent/grams | Overall-Yield |
|---|---|---|
| 1 | None | 4% |
| 2 | $NH_4I$/0.033 | 9.5% |

It is seen from the above data that ammonium iodide more than doubled the overall-yield for this reaction.

We claim:

1. A process for producing amines comprising reacting in the liquid phase ammonia or a primary or secondary amine with an olefin having one or more non-aromatic carbon to carbon double bonds in the presence of actinic light having an emission spectrum beginning above 160 nm and in contact with ammonium iodide or bromide photocatalyst whereby an N—H bond of the ammonia or amine is added across the double bond of the olefin.

2. The process of claim 1 wherein the photocatalyst is ammonium iodide.

3. The process of claim 1 wherein the photocatalyst is ammonium bromide.

4. The process of claim 1 wherein the olefin is an alkene having from 2 to 18 carbon atoms.

5. The process of claim 1 wherein the N—H containing reactant is ammonia or a mono- or dialkylamine where the alkyl groups have from 1 to 6 carbon atoms.

6. The process of claim 1 wherein the reaction is carried out in the presence of an effective amount of an inert solubilizing agent for the olefin reactant.

7. The process of claim 1 wherein the reaction pressure ranges from about 0 to about 500 psig.

8. The process of claim 1 wherein the reaction is carried out in a reactor vessel having amorphous silica glass walls.

9. The process of claim 2 wherein the N-H containing reactant is ammonia or a mono— or dialkylamine where the alkyl groups have from 1 to 6 carbon atoms.

10. The process of claim 9 wherein the olefin is an alkene having from 2 to 18 carbon atoms.

11. The process of claim 10 wherein the reaction is carried out in a reactor vessel having amorphous silica glass walls.

* * * * *